(12) United States Patent
Yoshifusa et al.

(10) Patent No.: US 9,205,449 B1
(45) Date of Patent: Dec. 8, 2015

(54) HEATING METHOD AND HEATING APPARATUS

(75) Inventors: Yuuki Yoshifusa, Fujinomiya (JP); Yutaka Itou, Fujinomiya (JP); Hiraku Murayama, Fujinomiya (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 159 days.

(21) Appl. No.: 12/631,535

(22) Filed: Dec. 4, 2009

Related U.S. Application Data

(63) Continuation of application No. 12/562,208, filed on Sep. 18, 2009, now abandoned.

(60) Provisional application No. 61/098,295, filed on Sep. 19, 2008.

(51) Int. Cl.
 *B05C 3/00* (2006.01)

(52) U.S. Cl.
 CPC .................. *B05C 3/00* (2013.01)

(58) Field of Classification Search
 CPC .............. B05C 3/00; G21G 5/00; H05B 9/06; H05B 1/00; A61K 31/4745; B29C 35/08
 USPC ........... 250/492.1; 219/10.55, 365, 342, 367, 219/368, 370, 377; 264/494; 424/423; 427/2.1, 2.24, 2.25
 See application file for complete search history.

(56) References Cited

U.S. PATENT DOCUMENTS

| | | | | |
|---|---|---|---|---|
| 3,854,024 A | * | 12/1974 | Kaufman et al. | 219/684 |
| 5,855,837 A | * | 1/1999 | Scranton et al. | 264/494 |
| 2005/0175660 A1 | * | 8/2005 | Mollison et al. | 424/423 |
| 2008/0078946 A1 | * | 4/2008 | Yamada et al. | 250/492.1 |
| 2008/0119762 A1 | | 5/2008 | Tateishi et al. | |

FOREIGN PATENT DOCUMENTS

| JP | 2006-320638 A | 11/2006 |
|---|---|---|
| JP | 2008-86575 A | 4/2008 |
| JP | 2008-125523 A | 6/2008 |

* cited by examiner

*Primary Examiner* — Dah-Wei D Yuan
*Assistant Examiner* — Andrew Bowman
(74) *Attorney, Agent, or Firm* — Buchanan Ingersoll & Rooney PC

(57) ABSTRACT

A method of manufacturing an elongated medical body coated with a fluororesin involves applying the fluororesin to the outer surface of an elongated body having a metallic substrate, and heating the elongated body with the fluororesin applied through operation of a heat source, while cutting off direct radiation of infrared rays generated from the heat source.

7 Claims, 11 Drawing Sheets

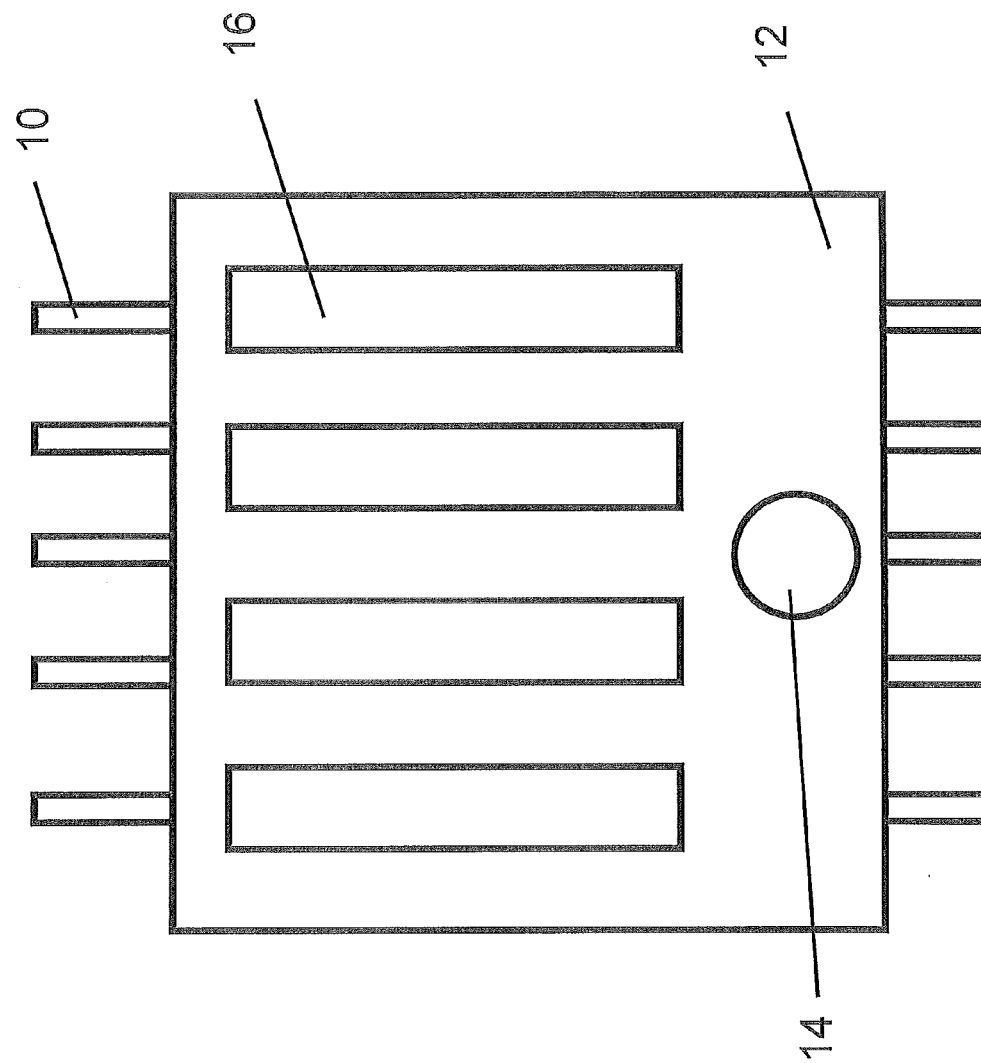

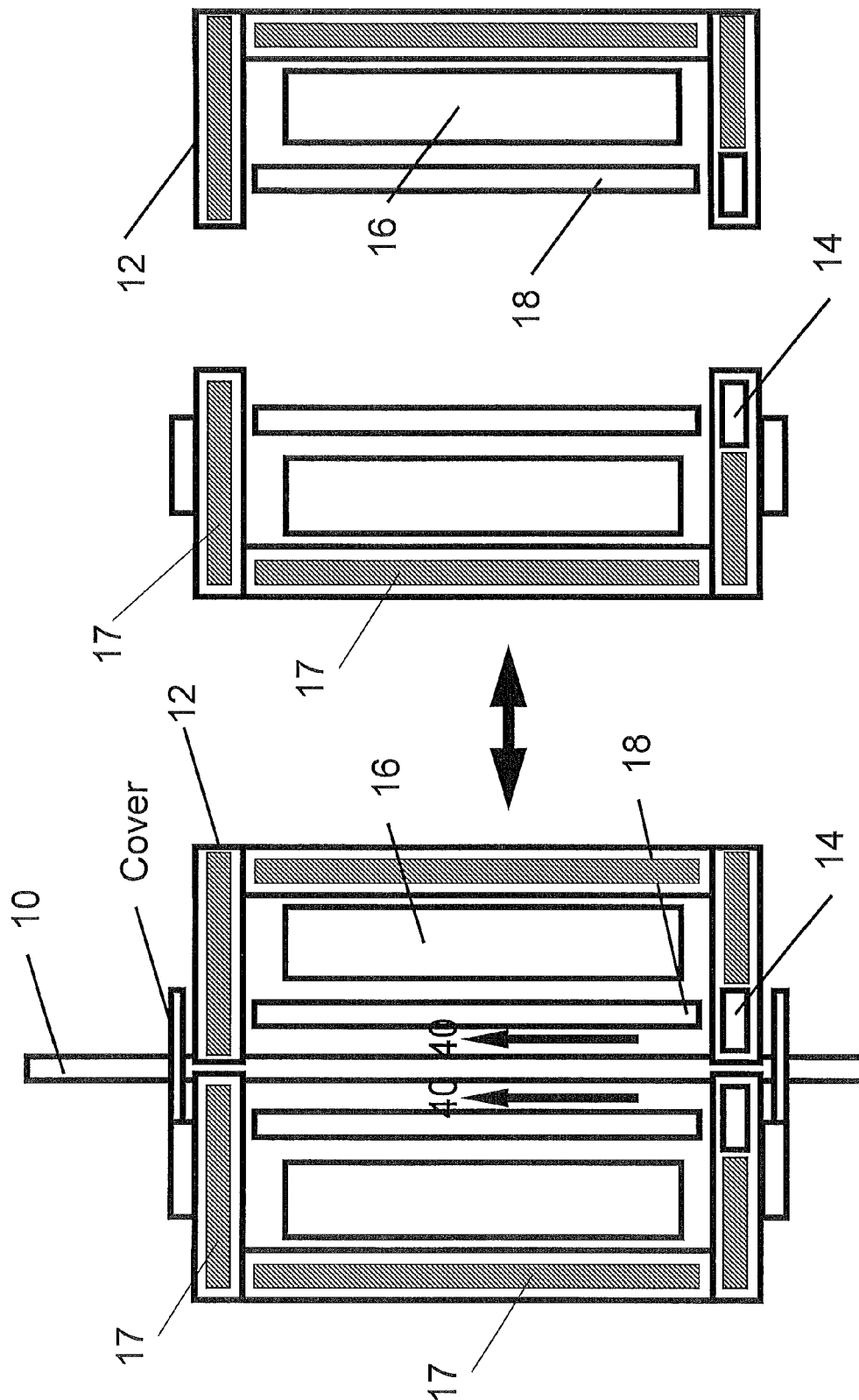

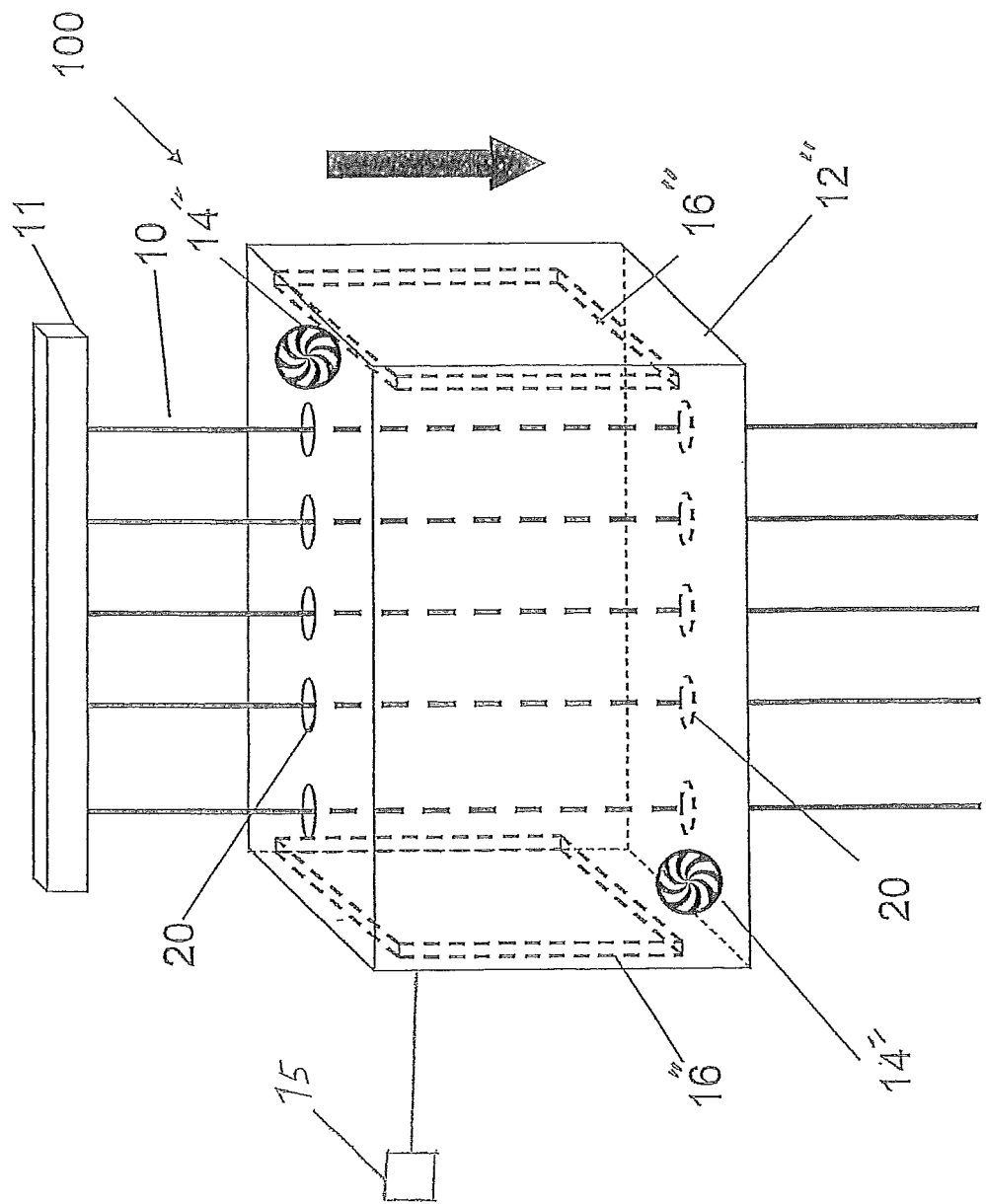

HEATING METHOD AND HEATING APPARATUS

This application claims priority under 35 U.S.C. §119(e) with respect to U.S. provisional Application No. 61/098,295 filed on Sep. 19, 2008, the entire content of which is incorporated herein by reference.

TECHNOLOGICAL FIELD

The present invention generally relates to the manufacture of an elongated medical body coated with a fluororesin. More specifically, the invention pertains to a heating method and a heating apparatus by which a resin is fixed onto the surface of a medical body having, for example, an elongated shape.

BACKGROUND DISCUSSION

Japanese Patent Laid-Open No. 2008-125523 discloses coating the outer surface of a medical body with a fluororesin for obtaining enhanced sliding properties. The fluororesin can normally be fixed onto the outer surface of a substrate member of a guide wire by burning the resin at a temperature (350 to 400° C.) not lower than its melting point. In carrying out a fluororesin burning treatment by an existing circulating hot air oven, the intended uses may include drying a medical body (work), fixation of a resin or other coating onto a metal, and extension or straightening of a medical body by heat.

It has been believed that burning a fluororesin by an existing circulating hot air oven makes it difficult to protect a metallic substrate wire inside a medical body from thermal energy (see, for example, Japanese Patent Laid-Open Nos. 2008-86575 and 2006-320638). Specifically, it has been believed that if temperature is raised to the melting point of the fluororesin, the characteristic properties of the metallic substrate being coated with the fluororesin would be spoiled or lost. For example, where the metallic substrate of the medical body is composed of a superelastic alloy, it has been thought that the superelasticity of the superelastic alloy wire is lost by such heating. In addition, the use of an existing circulating hot air oven may involve a number of other problems such as summarized below.

In one respect, the number of works that can be placed in the oven is limited, and the flow of hot air leads to swinging of the works and eventually to mutual contact of the works or dropping of the works.

Opening/closing of the oven door causes a temperature fall, and the starting temperature varies or is scattered according to the door-open time, so that the treating conditions vary.

Additionally, setting the work(s) is troublesome, and in situations where the treatment is repeated a number of times, especially, in the case where the work is long, other storage space(s) is needed, and the cooling time during when the work(s) is placed outside the oven varies or is scattered.

The openable door is so large that a human can enter the oven, which is dangerous.

Also, notwithstanding the forced circulation, the temperature rise gradient at the rise time is gentle, and thermal efficiency is often low, so that much energy is consumed in warming up the apparatus itself.

Further, where the work is relatively large or long, the apparatus must also be relative large in size and high in cost.

SUMMARY

According to one aspect, a method of manufacturing an elongated medical body coated with a fluororesin involves applying the fluororesin to the outer surface of an elongated member comprised of a metallic substrate, and heating the elongated member with the applied fluororesin through operation of a heat source. The heating of the elongated member includes heating the elongated member with the applied fluororesin while cutting off direct radiation of infrared rays generated from the heat source so the elongated member with the applied fluororesin is not directly irradiated by the infrared rays generated by the heat source.

Preferably, the heating of the elongated member involves applying circulation of hot air to the elongated member.

The circulated hot air may be applied from the lower side in relation to a longitudinal axis of the long body, or may be applied from the upper side in relation to the longitudinal axis of the elongated member.

The application of the fluororesin to the outer surface of the elongated member involves applying to the elongated member a fluororesin suspension containing a powder of the fluororesin suspended in a liquid or a step of applying a powder of the fluororesin directly to the elongated member.

The fluororesin may be at least one fluororesin selected from the group consisting of polytetrafluoroethylene (PTFE), tetrafluoroethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE).

Preferably, the metallic substrate is a superelastic alloy wire or a superelastic alloy wire coated with a synthetic resin.

The elongated medical body is a medical guide wire.

According to another aspect, a method of fixing fluororesin on the surface of an elongated medical body includes applying the fluororesin to the outer surface of an elongated member having a metallic substrate, heating the elongated member with the fluororesin applied through use of infrared rays, and cutting off direct application of the infrared rays to the elongated member with the fluororesin applied so that the infrared rays do not directly act on the elongated member with the fluororesin applied.

In accordance with another aspect, a method of manufacturing an elongated medical body coated with a fluororesin comprises applying the fluororesin to the outer surface of an elongated core member comprised of a metallic substrate to produce a coated elongated member possessing an outer surface of the fluororesin, relatively moving the coated elongated member and a heating unit comprised of an infrared ray-emitting heat source that emits infrared rays, emitting infrared rays from the infrared ray-emitting heat source during relative movement of the heating unit and the coated elongated member, and heating the coated elongated member by way of heat resulting from the infrared rays emitted by the infrared ray-emitting heat source. The coated elongated member is heated to a temperature equal to or greater than a melting temperature of the fluororesin. In addition, the method involves shielding the coated elongated member from direct radiation by the infrared rays during the heating by a barrier positioned between the infrared ray-emitting heat source and the coated elongated member.

An apparatus for fixing fluororesin on a surface of an elongated member to produce an elongated medical body comprises a heat source, a heat insulating section disposed on one side of the heat source and surroundingly opposed to the heat source so that a space exists between the heat insulating section and the heat source, a barrier disposed on a side of the heat source opposite the heat insulating section, the barrier being opposed to the heat source so that a space exists between the barrier and the heat source, the barrier being operative to cut off infrared rays generated by the heat source from being directly applied to the elongated member, and a fan by which hot air generated by the heat source is fed to a side of the barrier opposite the heat source. The apparatus is movable parallel to a longitudinal axis of the elongated member.

In accordance with the method and apparatus disclosed here, even where the elongated medical body is subjected to burning at a temperature of not lower than the melting point of the fluororesin, it is possible to obviate the situation in which the metallic substrate being coated with the fluororesin might loose its characteristic properties due to heating thereof. The elongated medical body with the fluororesin applied is heated by hot air while substantially cutting off infrared rays, whereby the loss of characteristic properties of the metallic substrate due to heating can be avoided while achieving the fluororesin coating. Specifically, hot air may be applied from the lower side relative to the longitudinal axis of the long body while cutting off infrared rays, whereby the hot air is fed in the form of a laminar flow, and the long body can be prevented from being swung. The hot air may be applied from the upper side relative to the longitudinal axis of the long body while substantially cutting off infrared rays, whereby heat can be kept stable in the vicinity of the elongated medical body.

BRIEF DESCRIPTION OF THE DRAWINGS

FIG. 5a is a side view of another embodiment of the heating apparatus disclosed here.

FIG. 5b is cross-sectional side view of the heating apparatus shown in FIG. 5a.

FIG. 5c is a cross-sectional top view of the heating apparatus shown in FIG. 5a.

FIG. 5d is a cross-sectional side view of the heating apparatus shown in FIG. 5a illustrating the heating unit in an open state in which the distance between the heating units is increased.

FIG. 6a is a perspective view of another example of a heating apparatus disclosed here.

FIG. 6b is cross-sectional side view of the heating apparatus shown in FIG. 6a.

FIG. 6c is a cross-sectional top view of the heating apparatus shown in FIG. 6a.

FIG. 6d is a cross-sectional top view of an alternative to the embodiment of the heating apparatus shown in FIG. 6a.

DETAILED DESCRIPTION

Figure 1:
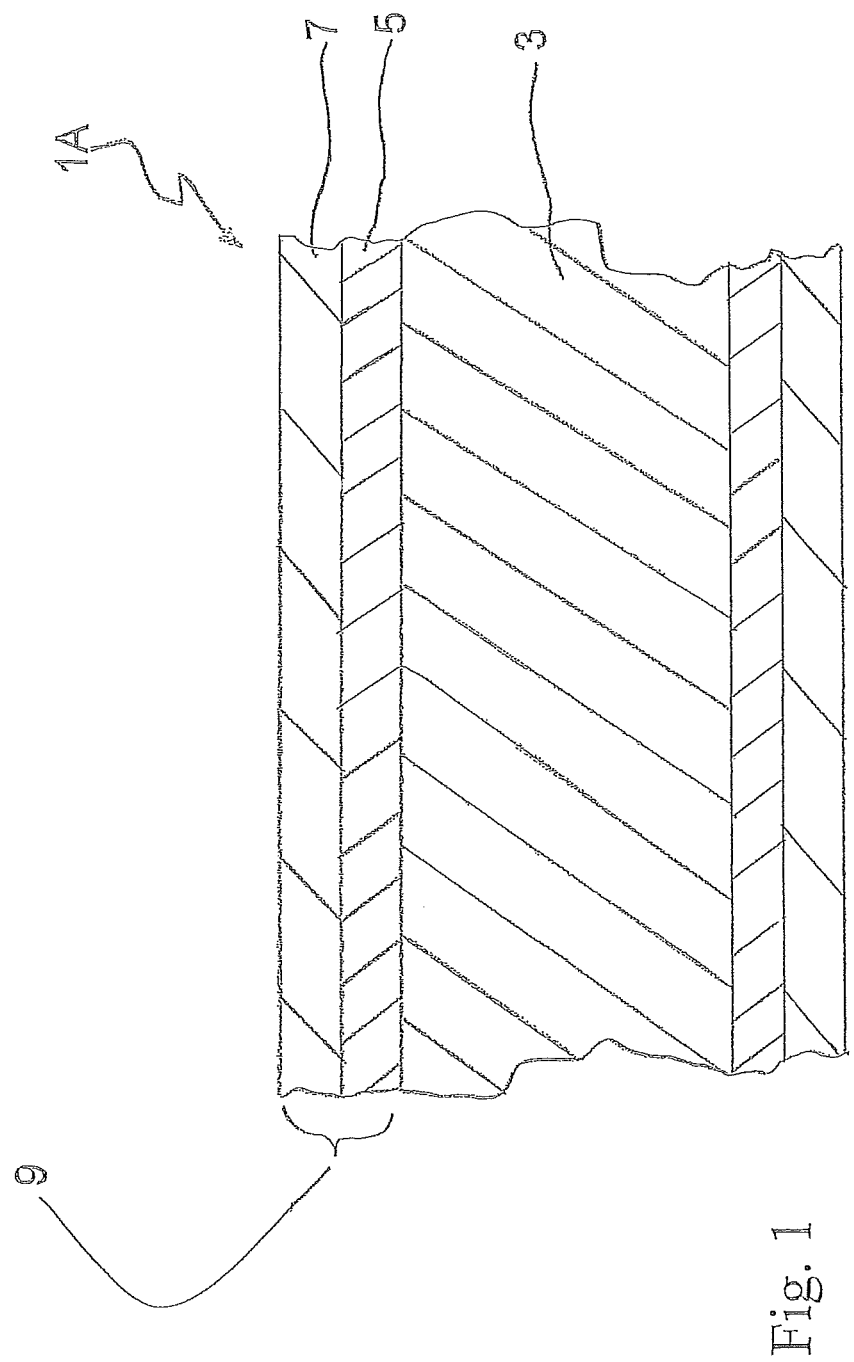
FIG. 1 is a longitudinal cross-sectional view of a portion of an elongated medical body disclosed here, manufactured by the method and apparatus disclosed here.

Set forth below is a detailed description of an elongated medical body manufactured by the manufacturing method and apparatus disclosed here. The elongated medical body may be, for example, a medical guide wire.

The elongated medical body 1A is an elongated medical body provided with a resin coating 9, preferably representing the outermost surface of the elongated medical body 1A. The elongated medical body 1A includes a substrate or core wire 3, a first resin layer 5 provided on at least a part of the surface of the substrate 3 so that the first resin layer 5 contacts the outer surface of the substrate 3, and a second resin layer 7 provided as a coating on the outer surface of the first resin layer 5 so that the second resin layer 7 contacts the outer surface of the first resin layer 5. The second resin layer 7 constitutes the outer surface (outermost surface of the elongated medical body 1A. In this disclosed embodiment, the resin coating 9 is comprised of the first resin layer 5 and the second resin layer 7. As described in more detail below, the method and apparatus disclosed here are described in the context of heating the resin coating 9.

The material of the substrate 3 is not particularly limited, and a variety of materials can be used as the material. Specific examples of the material of the substrate 3 include superelastic alloys, for example, a nickel-titanium (Ni—Ti) alloy. The Ni—Ti alloy may contain a minute amount of copper (Cu) and/or cobalt (Co) insofar as superelasticity of the alloy is maintained.

The shape of the substrate 3 is not particularly limited, and various shapes can be employed. Specific examples of the shape of the substrate include: a wire shape, a tubular shape such as pipe and a tube; a flat plate shape; a string-like shape; and three-dimensional shapes. Further, the substrate 3 is preferably a Ni—Ti alloy wire or a Ni—Ti alloy pipe. In the example in which the substrate 3 is a wire, its diameter is preferably about 0.1 to 10 mm, more preferably about 0.2 to 1.0 mm, though it is not limited in this regard.

The first resin layer 5 is provided at least on part of the outer surface of the substrate 3. The first resin layer 5 preferably contains a fluororesin. The fluororesin is preferably at least one selected from the group consisting of polytetrafluoroethylene (PTFE), tetrafluoroethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE).

The thickness of the first resin layer 5 is 1.0 to 3.0 µm, preferably 1.5 to 2.5 µm.

The method for forming the first resin layer 5 at least on part of the surface of the substrate 3 is not particularly limited. For instance, the first resin layer 5 can be formed by applying a coating solution (suspension) of the resin constituting the first resin layer 5 to a predetermined part of the surface of the substrate 3 (i.e., the part of the outer surface of the substrate 3 to be covered by the first resin layer 5), followed by drying. Alternatively, a powder of the resin constituting the first resin layer 5 may be applied directly to the outer surface of the substrate 3. Other than these methods, a dipping method which is known in the art may be employed.

The average thickness of the second resin layer 7 is preferably 0.1 to 30 µm. Average thickness refers to the thickness determined by averaging the thickness at three randomly selected locations. If the average thickness is substantially less than 0.1 µm, the sliding properties of the product tend to be undesirably diminished. If the average thickness is substantially more than 30 µm, the second resin layer 7 might peel. The second resin layer 7 covers the entire outer surface of the first resin layer 5.

The method for forming the second resin layer 7 is also not particularly limited. For instance, the second resin layer 7 can be formed by coating the surface of the first resin layer 5 with particulates of the resin, followed by drying. By this method, the second resin layer 7 is formed as a smooth surface on the first resin layer 5.

For example, a coating solution of a resin powder comprised of particles having the same average particle diameter is prepared, and the coating solution is applied to the outer surface of the layer 5, followed by drying. Aside from this method, a dipping method which is known in the art may be employed. As described in more detail below, the resin coating 9 (i.e., the first and second resin layers 5, 7 in this disclosed embodiment) is thereafter burned by heating to a temperature not lower than the melting point of the resin, whereby the second resin layer 7 is fixed as an outermost layer to the first resin layer 5, and the first resin layer 5 is fixed to the core wire 3.

As for the average particle diameter of the resin particulates, the resin particulates are preferably a fluororesin powder having an average particle diameter of 3 to 30 μm. If the average particle diameter of the resin particulates is substantially less than 3 μm, the thickness of the second resin layer 7 may not be of a desirable thickness. If the average particle diameter is more than 30 μm, the second resin layer 7 may peel off from the first resin layer 5.

A third resin layer may be provided intermediately between the substrate 3 and the first resin layer 5. In such a case, the third resin layer is preferably composed of a thermoplastic resin such as polyurethane and polyethylene. When the third resin layer is composed of a thermoplastic elastomer, the flexibility of the elongated medical body 1A is not spoiled, which is preferable. Where the melting point of the resin particulates for forming the second resin layer 7 is higher than the melting point of the third resin layer, the first resin layer 5 exhibits a heat insulating function relative to the third resin layer at the time of heating the second resin layer 7, whereby the third resin layer can be inhibited or prevented from being deteriorated. The elongated medical body manufactured by the manufacturing method disclosed here may have a single resin layer, instead of the plurality of resin layers.

One aspect of the disclosed method of manufacturing the elongated medical body coated with the fluororesin involves applying the fluororesin to the outer surface of an elongated body having a metallic substrate. In order to fix the fluororesin to the surface of the elongated body, the method includes exposing the elongated medical body (work or workpiece) to hot air circulation. For this purpose, there is utilized a heating method in which a heat source is moved in the vertical direction along the longitudinal axis of the elongated body. More specifically, the heating method involves moving a heat source in the vertical direction and parallel to the elongated body while cutting off direct radiation of infrared rays generated from the heat source to the elongated body so the elongated body is shielded from direct radiation of the infrared rays.

Figure 2:
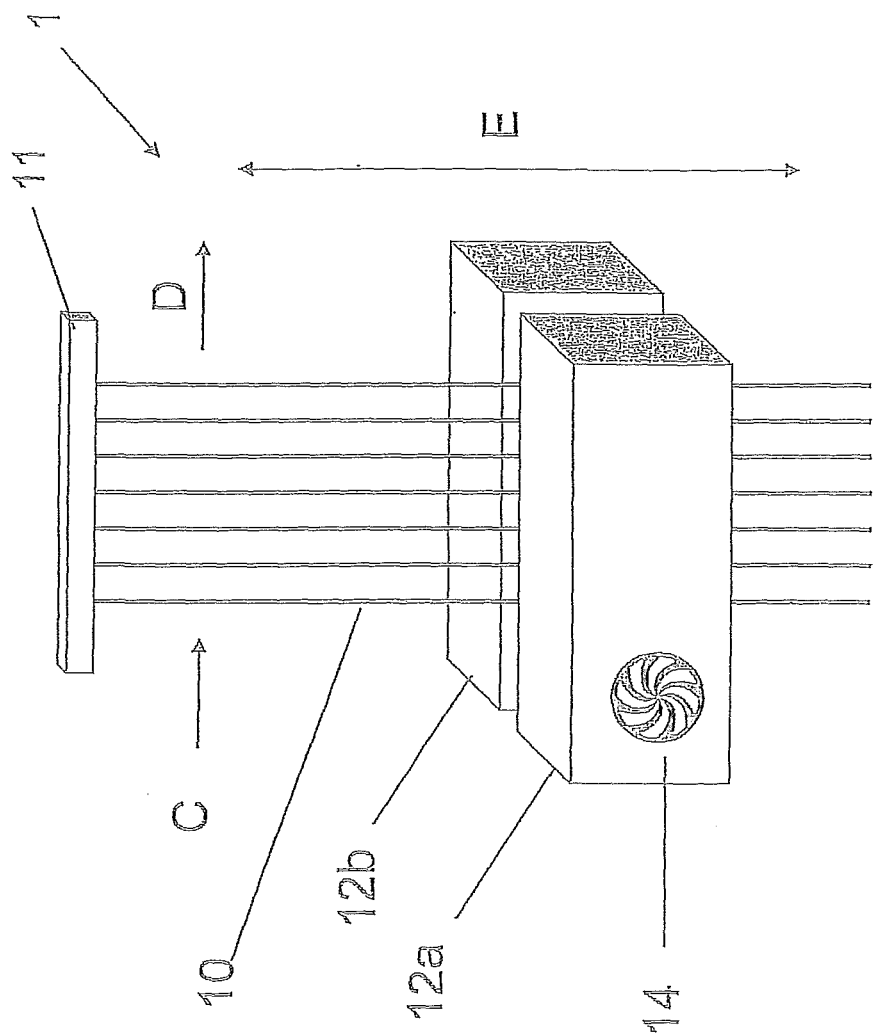
FIG. 2 is a perspective view of one embodiment of a heating apparatus disclosed here.

An example of a heating apparatus 1 which can be employed to carry out the method here is shown in FIG. 2. The heating apparatus includes a pair of heating units 12a, 12b. The first heating unit 12a and the second heating unit 12b each include a heat source(s). The first heating unit 12a and the second heating unit 12b are positioned on opposite sides of, and at a predetermined distance from, an elongated or long-shaped workpiece 10. The heating element 16 constituting the heat source may be a general heater, for example, an electric heater such as ceramic heater, thermal block heater, band heater, rod heater, quarts heater, nichrome wire heater, halogen heater, flexible heater, etc., a steam type heater such as steam heater, etc., an oil circulation type heater such as panel heater, etc., and a fuel type heater such as gas heater, light oil heater, etc.

Figure 3:
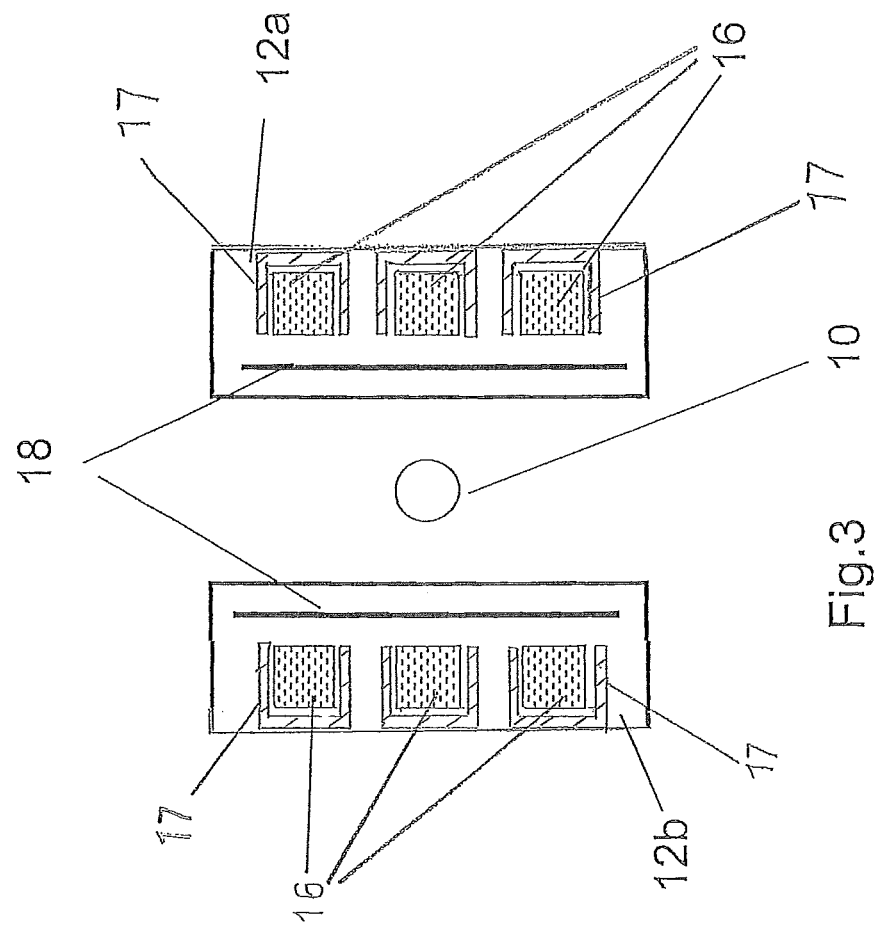
FIG. 3 is a cross-sectional view of a more specific embodiment of the heating apparatus disclosed here.

The heating units 12a, 12b each include a heat insulating material. Specifically, the heating element 16 of each heating unit 12a, 12b is surrounded by a heat insulating material. FIG. 3 illustrates by way of example heat insulting material 17 surroundingly opposed to the heating elements 16. The heat insulation 17 is preferably provided at upper and lower sides of each heating element 16, and at the back and lateral sides of each heating element 16. A space exists between the insulation 17 and the heating element 16, and between the insulation 16 and the barrier 18. The heating element 16 does not directly contact the insulating material 17 or the barrier 18. Thus, only the surface of the heating element 16 facing toward the barrier 18 is not bounded by (insulated by) the insulating material.

A plurality of workpieces 10 are mounted to and suspended from a mounting member 11 so that the workpieces are arranged or arrayed in a row at regular spaced intervals. Generally speaking, relative movement is effected between the workpieces 10 and the heating units 12a, 12b to perform the heating. More specifically, the first heating unit 12a and the second heating unit 12b, each comprised of the heat source(s), are moved in a direction along the length of the workpieces 10 (i.e., parallel to the length or longitudinal axis of the workpieces 10), while being spaced from the workpieces 10. In the illustrated embodiment, the first heating unit 12a and the second heating unit 12b are moved vertically up and down along the elongated workpieces 10, while being maintained at a predetermined distance from the elongated workpieces 10. The elongated works 10 are brought into the heating apparatus, with the first resin layer (and the second resin layer and/or the third resin layer) applied as above-mentioned.

The heat sources in the heating unit 12a and the heating unit 12b are general heaters which cause natural convection. The heating units may be of a circulating hot air type in which a fan 14 for forced circulation of the heat from the heat sources is incorporated. In the case of the circulating hot air type, the temperature is kept constant by agitation of air in the inside of the first heating unit 12a and the second heating unit 12b. The heat source is provided with means for cutting off infrared rays generated from the heat source. Therefore, the workpieces 10 are substantially not irradiated with the infrared rays generated from the heat sources. That is, the rays from the heating units are prevented from directly impinging upon the workpieces 10. In this case, natural convection due to heating may occur at upper portions of the first heating unit 12a and the second heating unit 12b. In the case where the natural convection influences the treatment of the workpieces 10, heat insulation by a heat insulating material as mentioned above or the like may be adopted, taking the treating conditions into account.

Further, the workpieces 10 after the treatment may be fed in the direction from C toward D in FIG. 2, i.e., in the direction in which the workpieces 10 are arrayed, whereby a treatment station for a required treatment, for example, cleaning or extension/straightening can be provided as a subsequent step. This helps ensure that the existing door opening and closing operations are eliminated, and the intermediate presence of a human is avoided, so that a continuous treatment can be carried out, the heating section is small in size and the apparatus can be disposed in a relatively compact form. Similarly, the workpieces 10 before the heating treatment can be fed to a position between the first heating unit 12a and the second heating unit 12b from the direction of the array of the workpieces 10, and can be stopped at predetermined positions.

Heat is applied by hot air to the resin coating on the surfaces of the workpieces 10 in the condition where the infrared rays are cut off so that the infrared rays will not act directly on the works 10. This helps ensure that the resin coating at the surfaces of the workpieces 10 can be melted and fixed in situ while being held at a temperature of not lower than the melting point of the resin. In this instance, the infrared rays which might otherwise cause the characteristic properties of the substrate metal of the workpieces 10 to be lost are cut off (shielded) from being directly applied to the workpieces 10, and so it is possible to inhibit or prevent loss of the superelasticity characteristics of the substrate metal.

FIG. 3 shows a more specific embodiment of the apparatus used here. To inhibit, and preferably prevent, the infrared rays generated by the heat sources from directly radiating onto the workpieces 10, a barrier member 18 for cutting off (shielding) the infrared rays is provided. The barrier 18 is positioned between the heating elements 16 of each heating unit 12a, 12b and the workpiece(s) 10. The barrier member 18 cuts off or shields the infrared rays. The barrier member 18 may be formed in a number of ways. For example, the barrier members 18 may be formed by a method in which an infrared ray barrier member, for example, is adhered to a surface facing the heating elements. More specifically, the infrared ray barrier member can be applied to the surface of a plate member in such a manner that the surface to which the barrier member is applied is a surface facing the heating units 12a, 12b. Alternatively, the barrier members may be formed by a method in which an infrared ray reflecting substance or an infrared ray absorbing substance is applied to the surface of a plate member (i.e., a surface facing the heating units). Another possibility for the barrier members 18 involves using barrier members with a surface having undergone a mirror finishing treatment. In this case, the barrier member 18 reflects (or absorbs) the infrared rays generated from the heat sources so that the infrared rays are inhibited or prevented from being radiated directly to or reaching the workpieces 10. In addition, by appropriately selecting the material and/or thickness of the barrier members 18, rays of specified wavelengths (for example, near infrared rays 0.7 to 4 µm, mid-infrared rays, far infrared rays 4 to 400 µm) can be selectively cut off (shielded).

Figure 4:
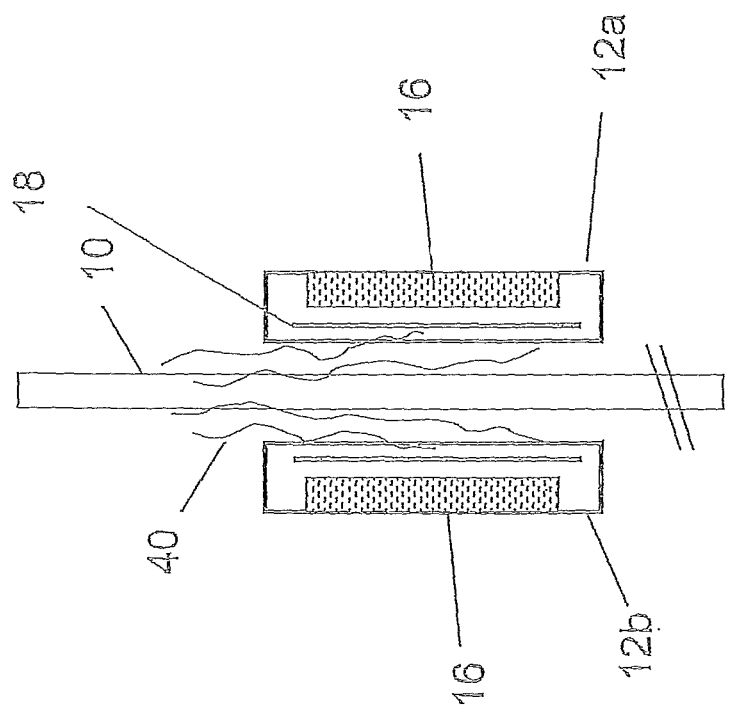
FIG. 4 is a cross-sectional view of another version of the heating apparatus disclosed here.

FIG. 4 shows a cross-section, as viewed sideways, of a heating apparatus by which heat from heating elements 16 is applied to a workpiece 10 in an open system. In this heating apparatus, direct radiation of infrared rays from the heating element 16 is cut off by the barrier members 18. In this case, the transfer of heat to the workpiece 10 is caused only by heat transfer from the heating elements 16 (through heating units) and by heat convection (hot air, natural convection 40). A specific example of this is an open system in which a certain space is present between the heating unit 12 and the workpiece 10. The space between the heating unit 12 and the workpiece 10 is such that heat transfer from the heating elements 16 can take place. No heat insulator for confining hot air is provided at upper and lower ends of the heating unit. In cases where the workpiece 10 itself is slender or flexible, or where it is desired to avoid strong impingement of air on the surface of the workpiece 10, it is preferable to realize heating in an open system such as shown in FIG. 4 by heat transfer from the heating elements 16 and by natural convection 40. The natural convection 40 is applied from the lower side relative to the workpiece 10 (elongated medical body). Therefore, the hot air in the natural convection 40 forms a laminar flow, whereby the elongated medical body is inhibited or prevented from being swung.

Figure 5C:
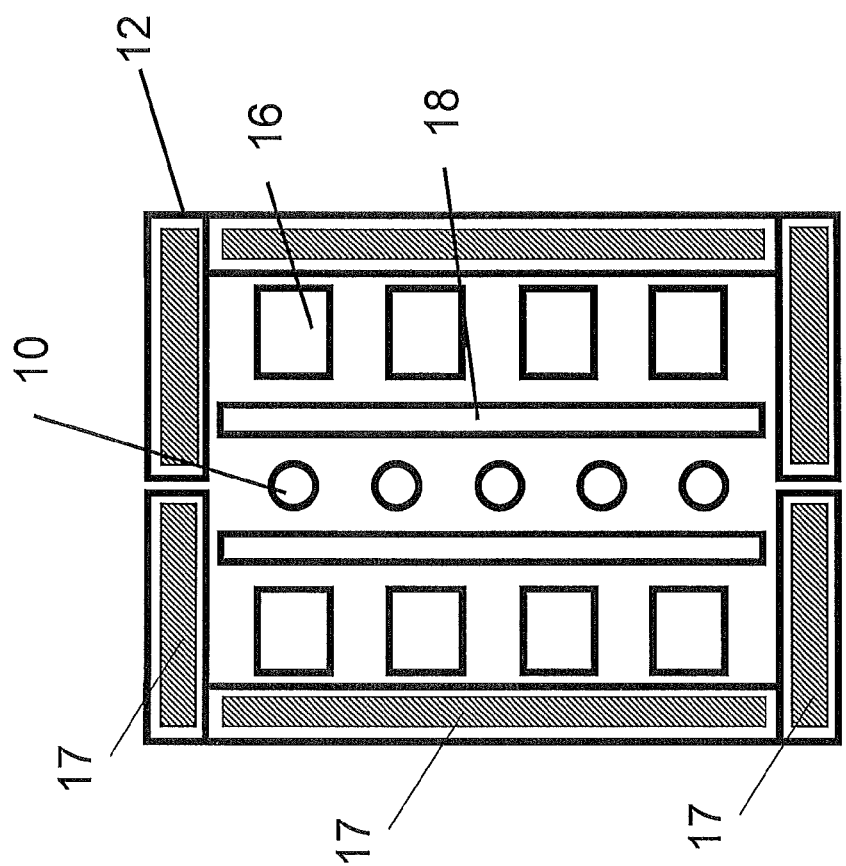

FIGS. 5a-5d show another embodiment of the apparatus disclosed here. In this embodiment of the apparatus for fixing a fluororesin onto the surface of an elongated medical body, the apparatus includes: a heat source; a heat insulating section disposed on one side of the heat source and surroundingly opposed to the heat source to form a space between itself and the heat source; a barrier member disposed on the other side of the heat source, opposed to the heat source to form a space between itself and the heat source, and operative to substantially cut off direct radiation of infrared rays onto the workpieces; and a fan by which hot air generated by the heat source is fed to the opposite side of the barrier member from the heat source, wherein the apparatus is moved parallel to the direction of the longitudinal axis of the elongated medical body. The heat insulating sections or heat insulations 17 are illustrated in FIGS. 5b-5d and are positioned inside the respective heating units 12a', 12b', with a space between the heat insulating sections 17 and the respective heating element. The heat insulating sections 17 are positioned at upper and lower sides of the space enclosing the heating elements 16, and at sides of the space so that the heat insulating sections surround the space enclosing the heating elements 16.

FIGS. 5a and 5b show in cross-section, as viewed from the side, the heating apparatus by which heat from heating elements 16' is applied to the workpieces 10 in a closed system. In this heating apparatus, direct radiation of infrared rays from the heating elements 16' is substantially cut off by the barrier members 18. In other words, the barrier members 18' prevent direct radiation onto the workpieces 10 of the infrared rays generated by or emanating from the heating elements 16'. A plurality of heating units 12a', 12b' are opposed to each other as shown in FIGS. 5b and 5c to intercept a certain degree of flow of heat from the surrounding environments, whereby a heating method in a closed system is provided. FIG. 5c shows the heating apparatus illustrated in FIGS. 5a and 5b, as viewed from above. The infrared rays from the heating elements 16' are cut off by the barrier members 18', and are thus prevented from being directly applied to the workpieces 10. In this case, hot air generated by the heating elements 16' is forcibly fed in a circulating manner to the workpiece 10 side of the heating units by fans 14' provided at lower portions of the heating units. The hot air thus blown is fed into the space surrounding the workpieces 10 to heat the workpieces 10. Circulation of the hot air can be promoted by blowing the hot air from the inside spaces of the heating units to the exterior by fans provided at upper portions of the heating units. Fans at the upper portions of the heating units can also help upwardly draw air from the lower parts of the heating units. These fans at the upper portions of the heating units can be positioned in the same manner at the upper portions of the heating units as the illustrated heating units 14' at the lower portions of the heating units as shown in FIGS. 5a' and 5b'.

With the hot air driven (applied) from the lower side relative to the workpieces 10, the hot air in the forced convection 40 forms a laminar flow, whereby the medical elongated bodies can be prevented from swinging. In addition, the fans 14' provided at lower portions of the heating units can circulate air from the inside spaces of the heating units to the exterior, and, simultaneously, the fans provided at upper portions of the heating units can blow air from the exterior into the inside spaces of the heating units. In this case, it is possible to form convection directed from the upper side toward the lower side. The forced convection 40 directed from the lower side toward the upper side is inhibited from rising, so that heat is prevented from escaping upwards. Therefore, heat can be kept stable in the vicinity of the workpieces 10, and a comparatively constant temperature can be maintained. Such heating by forced convection is favorable in situations where a large number of workpieces are being heated or where more uniform heating is needed.

In the specific embodiment shown in FIGS. 5a-5d, the distance between the left and right heating units 12a', 12b' can be varied to vary the heating efficiency while restraining omission (escape) of heat by convection. With the left and right heating units 12a', 12b' set closest to each other as best shown in FIGS. 5b and 5c, the heating units 12a', 12b' substantially come into contact with each other at their facing side surfaces to form a closed heating system, whereby heat can be confined in the heating unit inside space. In this position or state of the heating apparatus, escape of heat can be restrained by providing covers at upper surfaces of the first heating unit 12a' and the second heating unit 12b' as shown in FIG. 5b. In the case of forced convection (hot air circulation) as in the embodiment shown in FIGS. 5a-5d, it is desirable to adopt a configuration in which the workpieces are passed through a required minimum gap between the left and right heating units or the heating units are set to overlap with each other, thereby narrowing the gap therebetween.

As represented by the arrow between FIGS. 5b and 5d, FIG. 5d illustrates the heating apparatus of FIG. 5b in a different state (open state or open system) in which the distance between the heating units is increased. One or both of the heating units can be outfitted with an appropriate drive device to relatively move the heating unit(s) toward or away from one another and thereby vary the distance between the heating units to vary the heating efficiency or amount of heating which takes place, and to switch the open system to the closed system and vice versa. The embodiment shown in FIGS. 5b-5d includes insulating sections 17 inside the heating units. As illustrated, a space exists between the insulating sections 17 and the heating elements 16.

It should also be understood that another version of the apparatus is possible in which the apparatus is configured in the manner shown in FIGS. 5a-5c, but the heating units 12a', 12b' are not movable to adjust the distance between the heating units. In this alternative, the heating apparatus would remain a closed system (i.e., would be a permanently closed system). Similarly, in a further embodiment, an apparatus is configured in the manner shown in FIG. 5d, but the heating units 12a', 12b' are not movable to adjust the distance between the heating units. This embodiment would be one in which the heating apparatus forms a permanently open system Another version of the heating apparatus 100 shown in FIGS. 6a-6c includes a box-shaped closed-system heating unit 12" in which heating elements 16" and barrier members 18" are positioned inside the box-shaped enclosure (i.e., in the interior of the housing). Thus, the heating unit 12" is comprised of the housing enclosing or bounding a housing interior, the heating elements 16" positioned in the housing interior and barrier members 18"also located in the housing interior. In this heating apparatus, infrared rays generated directly from the heating elements 16" are substantially cut off by the respective barrier members 18". In other words, the barrier members 18" prevent the infrared rays generated by the heating elements 16" from being radiated directly onto the workpieces 10. The barrier members 18" prevent direct irradiation of the workpieces 10 with the infrared rays generated by the heating elements 16". The barrier members 18" are disposed at predetermined positions between the heating elements 16" and the workpieces 10, to prevent irradiation of the workpieces 10 with the infrared rays. Opposite surfaces or sides of heating unit housing are provided with opening 20. In the illustrated embodiment, the upper and lower surfaces of the housing of the heating unit 12" are provided with openings 20. The openings 20 are sized to permit the elongated workpieces 10 to receive and pass through the openings. The elongated workpieces 10 are mounted to and suspended from a mount member 11 while arranged in an array or row (common plane) in which the elongated workpieces 10 are positioned at certain intervals (at different intervals or at regular/ common intervals).

The number of the openings 20 is equal to the number of the elongated workpieces 10 mounted to the mount member 11, and the interval or spacing between adjacent openings 20 is equal to the intervals or spacing between adjacent elongated workpieces 10. The interior of the housing of the heating unit 12" is provided with fans 14" by which the heat from the heating elements 16" is forcibly circulated (circulating hot air type).

Figure 6B:
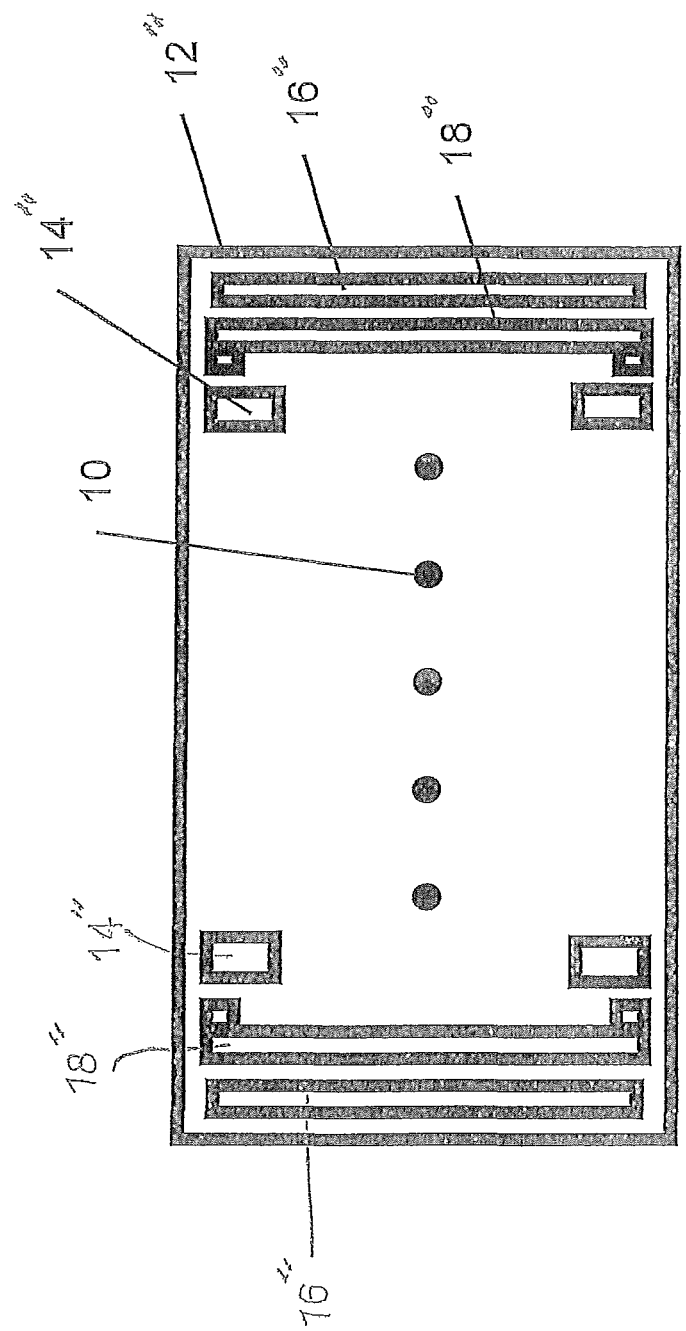
Figure 6C:
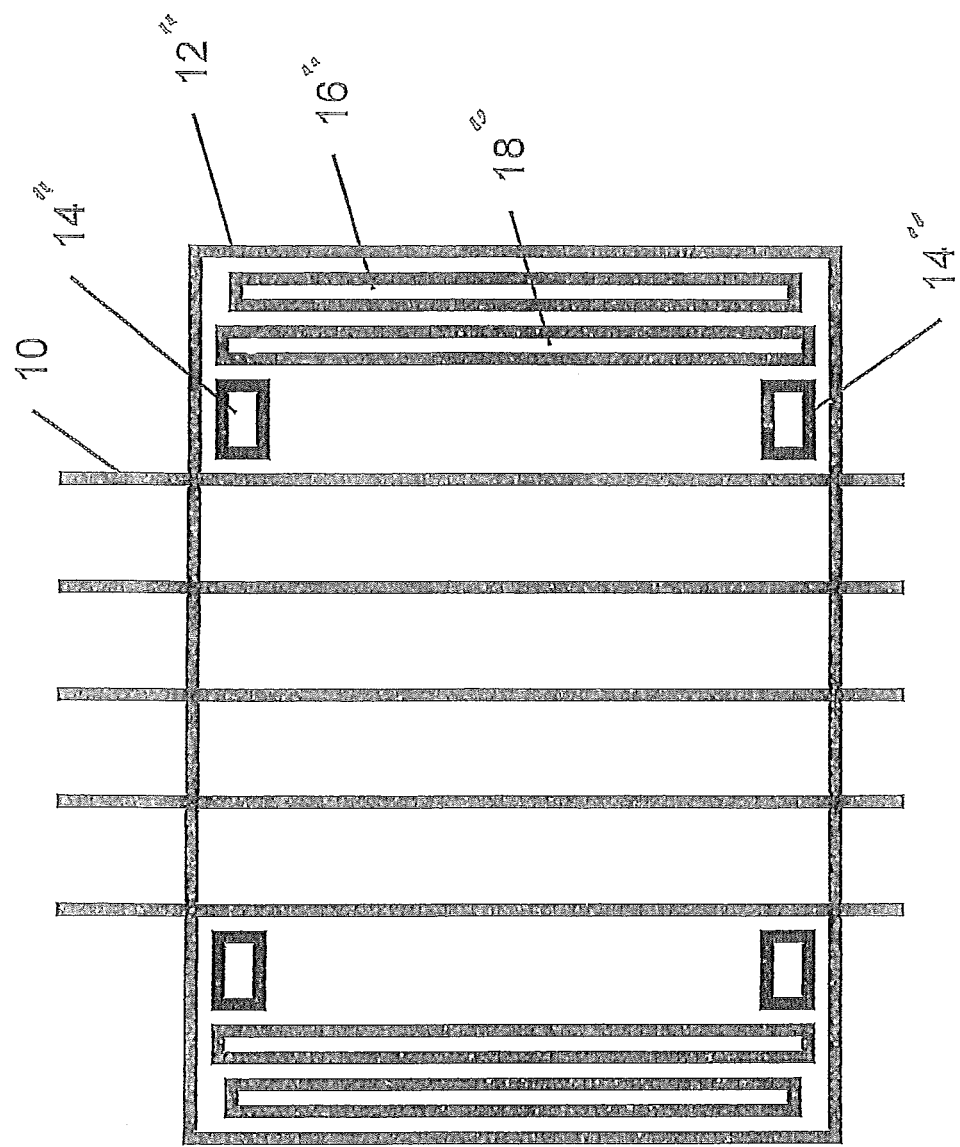

FIG. 6a shows some of the fans 14 "in the heating unit housing. FIGS. 6b and 6c illustrate more of the fans 14". The fans 14" are preferably positioned at comparatively lower portions of the interior of the heating unit housing and also at comparatively upper portions of the heating unit housing interior. In this heating unit, hot air can be circulated only in the inside of the heating unit by the fans. That is, the supply of air from outside the heating unit can be stopped, and air (hot air) can be circulated only in the inside of the heating unit. The forced convection (hot air flow) thus generated is applied to the workpieces 10 in the direction from the lower side toward the upper side or in the direction from the upper side toward the lower side. With the hot air driven toward (applied to) the workpieces 10 from the lower side, the hot air of the forced convection 40 forms a laminar flow, and so the elongated medical bodies are inhibited or prevented from swinging. Since a downwardly directed convection can be formed, a rise of forced convection from the lower side toward the upper side is inhibited, whereby upward escape of heat can be inhibited. Therefore, heat can be kept stable in the vicinity of the workpieces 10, and a comparatively constant temperature can be maintained.

The heating method disclosed here, using the heating apparatus 100 shown in FIGS. 6a-6c as an example, is described below. Initially, the heating unit 12" is positioned at a lowered position relative to the workpieces 10. Specifically, the heating unit 12" is located at a lowermost position and is positioned on the lower side of the workpieces 10 (or a space which will be occupied by the workpieces 10) in a condition where the workpieces 10 are not contained in the heater 12". The elongated workpieces 10 are mounted on the mount member 11 so that the elongated workpieces 10 are arranged or arrayed in a row at regular spaced intervals (or at different intervals) so that a predetermined distance is maintained between adjacent workpieces (i.e., the workpieces are fixed relative to the mount so the workpieces do not move along the mount).

The workpieces 10 are workpieces to which the resinous coating 9 (e.g., the first and second resin layers 5, 7, and possibly a third resin layer as described above) has been applied and dried. In connection with the disclosed embodiment of the workpiece 10, the first resin later 5 is applied to the core wire 3 and dried, and then the second resin layer 7 is applied on the dried first resin layer, and the second resin layer 7 is dried. This produces the workpieces or coated elongated members which are subjected to the heating method discussed below through use of the embodiments of the heating apparatus described above. To the extent the resinous coating 9 (e.g., the first and second resin layers) is subjected to heat to effect the drying, such heating is significantly less then the heating to which the workpiece is subjected by the disclosed heating apparatus and method to fix the resinous coating 9 (e.g., the first and second resin layers) as described below.

The drying of the resin layers 5, 7 involves temperatures that allow the solvent, in which the resin is dissolved, to vaporize while the resin remains on the outer surface of the workpiece. The drying temperature should not exceed the boiling point of the solvent to avoid damaging to the outer surface of the workpiece. The drying temperature is preferably at least 5° C.-10° C. below the boiling point of the solvent. The drying temperature should not exceed the melting point of the resin (e.g., PTFE), which melting point is typically greater than the boiling temperature of the solvent. On the other hand, the heating of the resinous coating though use of the apparatus and method disclosed here is performed at a temperature greater than the melting point of the resin in order to fix the resinous coating in place. The maximum temperature used to dry the resin layers 5, 7 is at least 10° C. less than the temperature to which the workpieces are subjected during the heating to fix the resinous coating 9 in place.

The elongated workpieces 10 mounted to the mount member 11 are positioned above, or on the upper side of, the heating unit 12" by, for example, being moved from the preceding drying step. That is, after the resinous coating 9 on the workpieces has been dried, the workpieces 10 can be moved into position above the heating unit 12". It is also possible to use the same mount 11 during drying that is subsequently used during heating in the heating unit 12". That is, the workpieces 10 can be mounted on a mount 11 and then subjected to drying while mounted on the mount. After drying the workpieces 10, the mount with the workpieces still mounted thereon can be moved to a position above the heating unit 12". The workpieces 10 are positioned so that the lower end portions of the elongated workpieces 10 are located substantially at centers of the openings 20. Subsequently, the heating unit 12" is moved upwards while the inside of the heater unit housing is kept at a predetermined temperature. The heating unit 12" can be moved in any appropriate manner. FIG. 6a schematically illustrates a driving system or moving means 15 operatively connected to the heating unit 12" to move the heating unit 12" relative to the workpieces 10 and the mount 11, in this embodiment to move the heating unit 12 vertically up and down.

As the heating unit 12" is moved, the elongated workpieces 10, starting from their lower ends, enter the inside of the heating unit housing through the openings 20 in the upper surface of the heating unit 12". The inside of the heating unit 12" is at a temperature raised by hot air circulated by the fans 14" so that surfaces of the elongated workpieces 10 are heated. The thus heated elongated workpieces 10 pass come out of the heating unit 12" through the openings 20 formed in the lower surface of the heating unit 12". The heating elements 16" may be disposed at locations near the opposite sides of the heating unit housing as generally shown in FIGS. 16a-16c. Alternatively, heating elements may be disposed between adjacent workpieces 10, with each heating element surrounded by a barrier or barrier members.

Figure 6D:
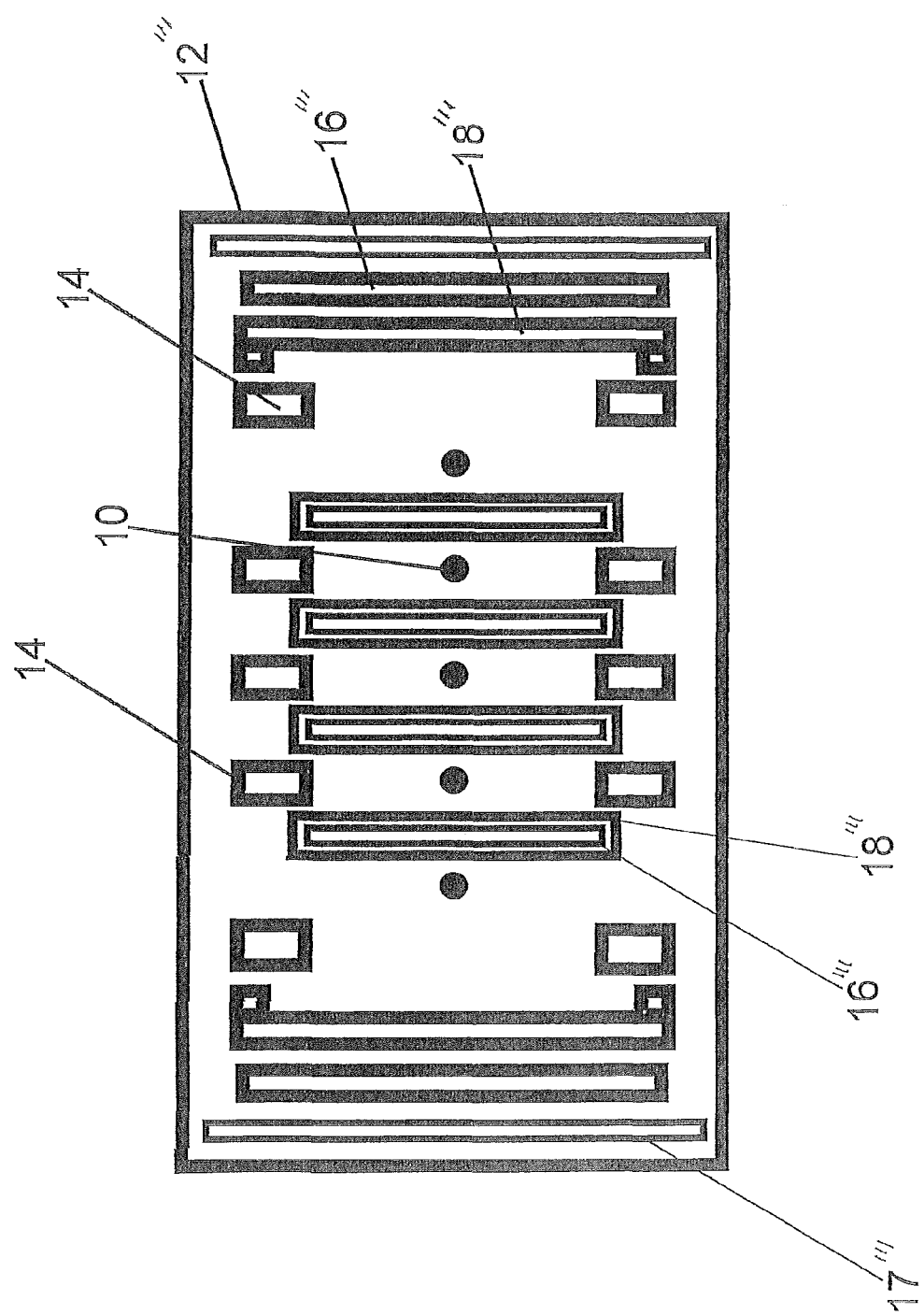

An example of such an alternative is shown in FIG. 6d. Here, a plurality of heating elements 16' is provided, each surrounded by a barrier 18'''. The heating elements 16" are positioned so that during heating, each workpiece is positioned between a different pair of heating elements 16'''. FIG. 6d also illustrates the insulating sections between the heating elements 16''' and the housing of the heating unit 12'. Spaces exist between each insulating section 17' and the heating elements 16''', and between the insulating section and the housing wall. As mentioned above, the barriers or barrier members 18''' inhibit or prevent the infrared rays from being radiated onto the workpieces 10.

When the heating unit 12" has been moved upwards into the vicinity of the upper ends of the elongated workpieces 10, the movement of the heater 12" is switched to a downward movement. Alternatively, once the heater 12" is stopped in the vicinity of the upper ends of the elongated workpieces 10, and after a predetermined period of time, downward movement of the heater 12" is initiated. When the lower ends of the elongated workpieces 10 have come out of the openings 20 in the upper surface of the heating unit 12", the movement of the heating unit 12" is stopped. To subject the elongated workpieces 10 to subsequent operations, the workpieces 10 can be dismounted or removed from the mount member 11, or they can be fed to the subsequent operation/step together with the mount member 11. Through these operations or steps, a resin layer is applied to and fixed on the workpieces 10.

By way of example, the driving system or moving means 15 for driving or moving the heating unit can be operated by a combination of a ball screw or a linear slider, an air cylinder or cylinders, sprockets and a chain, and the like.

The heating system using the heating apparatus 100 disclosed here helps ensure that the opening/closing of a door as in other known arrangements is eliminated, and the need for the intermediate presence of a human is avoided so that the treatments can be carried out continuously. The heating section is relatively small in size, the apparatus can be disposed in a compact form, the choice of the installation place for the apparatus is increased, and the apparatus is reduced in cost.

As mentioned above in connection with the embodiment shown in FIGS. 5a-5d, the heating units 12a', 12b' are movable between the closed position (closed system) shown in FIG. 5b and the open position (open system) shown in FIG. 5d. One manner of operating this disclosed embodiment of the heating apparatus involves initially positioning the heating units 12a', 12b' in the closed state best illustrated in FIG. 5b with power fed to the heating elements 16'. The closed state of the heating units 12a', 12b' allows the inside of the heating units 12a', 12b' to heat up. At this time, the heating units 12a', 12b' can be positioned below the lower end of the workpieces 10 which can be mounted on a mount similar to that shown in FIG. 6a. As the temperature inside the heating units 12a', 12b' increases, the heating units 12a', 12b' can be moved to the open position while also moving upward. This allows the workpieces 10 to be positioned between the heating units 12a', 12b'. As the heating units 12a', 12b' move upward, the heating elements 16' continue to be powered and continue to provide heat to the workpieces, though the workpieces 10 are shielded from direct infrared radiation generated by the heating elements 16' by virtue of the barriers 18. This upward movement of the heating units 12a', 12b' while in the open state results in a pre-heat process for the workpieces 10.

As the heating units 12a', 12b' reach the uppermost position, or as the heating units 12a', 12b' approach such position, relative movement between the heating units 12a', 12b' is again initiated to move the heating units 12a', 12b' towards each other until the closed state of the heating units 12a', 12b' shown in FIG. 5a is reached. The heating units 12a', 12b' then begin a downward descent relative to the workpieces 10. With the heating units 12a', 12b' closed and the heating elements 16' continuing to heat, more heat or stronger heat is provided to the workpieces 10, though the workpieces 10 remain shielded, by virtue of the barriers 18, from direct infrared radiation emanating from the heating elements 16'. The downward movement of the heating units 12a', 12b' while in the closed position (closed system) provides the main heating for the workpieces 10 that fixes the resinous coating.

It should be understood by those skilled in the art that various modifications, combinations, sub-combinations and alterations may be implemented depending on relevant factors. The principles, embodiments and modes of operation of the heater unit and method have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of manufacturing an elongated medical body coated with a fluororesin comprising:

applying the fluororesin to an outer surface of an elongated core member comprised of a metallic substrate to produce a coated elongated member possessing an outer surface of the fluororesin, the elongated core member being mounted to and vertically suspended from a mounting member;

relatively moving the coated elongated member and a heating unit comprised of an infrared ray-emitting heat source that emits infrared rays, the infrared ray-emitting heat source being positioned in an interior of a housing;

emitting infrared rays from the infrared ray-emitting heat source during relative movement of the heating unit and the coated elongated member;

heating the coated elongated member by way of heat resulting from the infrared rays emitted by the infrared ray-emitting heat source;

the coated elongated member being heated to fix the fluororesin to the elongated core member by applying a forced convection of hot air, generated by the infrared ray-emitting heat source, to the coated elongated member in a direction from an upper side of the coated elongated member toward a lower side of the coated elongated member or in a direction from the lower side of the coated elongated member toward the upper side of the coated elongated member, the forced convection of hot air being applied to the coated elongated member by operation of a fan positioned in the interior of the housing;

the heating of the elongated member comprising moving the heat source in a vertical direction and parallel to the elongated member;

the coated elongated member being heated to a temperature equal to or greater than a melting temperature of the fluororesin; and shielding the coated elongated member from direct radiation by the infrared rays during the heating by a barrier positioned between the infrared ray-emitting heat source and the coated elongated member.

2. The method according to claim 1, wherein the forced convection of hot air is applied to the coated elongated member by operation of a plurality of fans positioned in the interior of the housing.

3. The method according to claim 1, wherein the coated elongated member moves within the housing during the relative movement of the coated elongated member and the heating unit, and the barrier being positioned between the coated elongated member and the infrared ray-emitting heat source.

4. The method according to claim 1, wherein the applying of the fluororesin to the outer surface of the elongated member comprises: applying to the elongated member a fluororesin suspension containing a powder of the fluororesin suspended in a liquid or applying a powder of the fluororesin directly to the elongated member, and drying the fluororesin before the heating of the coated elongated member.

5. The method according to claim 1, wherein the fluororesin is at least one fluororesin selected from the group consisting of polytetrafluoroethylene (PTFE), tetrafluoroethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE).

6. The method according to claim 1, wherein the relative movement of the elongated member with the applied fluororesin and the heating unit comprises introducing the coated elongated member into the interior of the housing through a hole in one side of the housing, the coated elongated member moving out of the interior of the housing by way of another hole in an opposite side of the housing.

7. The method according to claim 1, wherein the elongated medical body is a medical guide wire.

* * * * *